United States Patent [19]

Bell

[11] Patent Number: 5,099,859
[45] Date of Patent: Mar. 31, 1992

[54] METHOD AND APPARATUS FOR COMPARATIVE ANALYSIS OF VIDEOFLUOROSCOPIC JOINT MOTION

[76] Inventor: Gene D. Bell, 3270 Brockton Common Dr., Florissant, Mo. 63031

[21] Appl. No.: 280,566

[22] Filed: Dec. 6, 1988

[51] Int. Cl.⁵ .................................................. A61B 5/103
[52] U.S. Cl. .................................... 128/781; 128/782; 378/42; 378/154
[58] Field of Search .............. 128/774, 779, 781, 782, 128/653; 378/41, 42, 147, 148, 154, 155, 174-176, 179, 190, 192, 99, 177, 195, 208; 357/111

[56] References Cited

U.S. PATENT DOCUMENTS

| | | | |
|---|---|---|---|
| 1,551,162 | 8/1925 | Loebell | 378/154 |
| 2,552,592 | 5/1951 | Rush | 378/208 |
| 2,739,257 | 3/1956 | Sheldon | 358/111 |
| 2,760,077 | 8/1956 | Longini | 378/154 |
| 2,824,970 | 2/1958 | Ledin | 378/154 |
| 3,091,692 | 5/1963 | Verse | 250/61.5 |
| 3,675,012 | 7/1972 | Derderian et al. | 250/60 |
| 3,769,507 | 10/1973 | Kenney et al. | 250/52 |
| 4,039,841 | 8/1977 | Leighley | 378/154 |
| 4,101,961 | 7/1978 | Reiber | 128/653 |
| 4,182,316 | 1/1980 | Nilsson et al. | 128/665 |
| 4,209,706 | 6/1980 | Nunan | 250/490 |
| 4,245,244 | 1/1981 | Lijewski et al. | 358/111 |
| 4,295,473 | 10/1981 | Diamond et al. | 178/695 |
| 4,383,328 | 5/1983 | Kurihara et al. | 378/42 |
| 4,393,402 | 7/1983 | Keyes et al. | 378/99 |
| 4,416,293 | 11/1983 | Anderson et al. | 128/782 |
| 4,437,161 | 3/1984 | Anderson | 364/414 |
| 4,450,478 | 5/1984 | Ledley | 358/111 |
| 4,458,267 | 7/1984 | Dolazza | 358/111 |
| 4,483,342 | 10/1984 | Pfeifer | 128/653 |
| 4,532,546 | 7/1985 | Aufiero et al. | 358/111 |
| 4,533,947 | 8/1985 | Smith | 358/111 |
| 4,538,227 | 8/1985 | Toraichi et al. | 364/414 |
| 4,549,555 | 10/1985 | Fraser et al. | 128/782 |
| 4,563,701 | 1/1986 | Gilath et al. | 358/111 |
| 4,577,222 | 3/1986 | Kruger et al. | 358/111 |
| 4,598,368 | 7/1986 | Umemura | 364/414 |
| 4,600,012 | 7/1986 | Kohayakawa et al. | 128/665 |
| 4,616,319 | 10/1986 | Peters et al. | 364/414 |
| 4,631,676 | 12/1986 | Pugh | 364/413 |
| 4,655,227 | 4/1987 | Gracovetsky | 128/781 |
| 4,674,107 | 6/1987 | Urban et al. | 378/98 |
| 4,845,747 | 7/1989 | Koike et al. | 378/208 |
| 4,858,126 | 8/1989 | Croce, Jr. | 128/774 |
| 4,937,859 | 6/1990 | Hubert et al. | 378/154 |

FOREIGN PATENT DOCUMENTS

| | | | |
|---|---|---|---|
| 0245098 | 11/1987 | European Pat. Off. | 128/781 |
| 0145492 | 12/1978 | Japan | 128/653 |
| 0772529 | 10/1980 | U.S.S.R. | 128/781 |
| 0882516 | 11/1981 | U.S.S.R. | 128/633 |
| 1191064 | 11/1985 | U.S.S.R. | 128/779 |

OTHER PUBLICATIONS

Johnson, F. et al., *Method for Routine Clinical Accessment of Knee-Joint Forces*, Med & Biol. Eng. & Comput., 17, No. 2, 145-154 (1979).

(List continued on next page.)

Primary Examiner—Lee S. Cohen
Assistant Examiner—Scott R. Akers
Attorney, Agent, or Firm—Richard G. Heywood; Frank R. Agovino

[57] ABSTRACT

Apparatus and method for generating successive video images of a moving bone of a subject. A fluoroscope generates a fluoroscopic image of the moving bone. A video camera detects the fluoroscopic image and converts the detected image into successive video images. A recorder records the successive video images. A monitor displays the recorded successive video images as the images are being generated. The monitor is located adjacent the fluoroscope for viewing by an operator thereby permitting the operator to observe and/or position the bone in response to images displayed on the monitor. A crisscrossed grid is located adjacent the image intensifier of the fluoroscope between the bone and the image intensifier. A CPU compares the successive video images to a reference representation corresponding to a desired or previous movement or pattern of movement of the bone with respect to a second, immobilized bone and any resulting flexure of a joint between the bone and the second, immobilized bone.

42 Claims, 3 Drawing Sheets

OTHER PUBLICATIONS

Panjabi, M. M. et al., *A Technique for Measurement*, J. Biomechanics vol. 14, No. 7, 447-60 (1981).

Squire, L. F., *Fundamentals of Radiology*, Harvard University Press 1975, pp. 296, 298, 290.

Computer Graphics Research in Chiropractic Comes of Age, Solomon J. Herbert, Ica International Review of Chiropractic, Fall 1985, pp. 25-27.

The Fundamentals of Computer Aided X-Ray Analysis of the Spine, C. H. Suh, Journal of Biomechancis, 1974, vol. 7, pp. 161-169.

Three-Dimensional Mathematical Model of the Human Spine Structure, M. Panjabi, Journal of Biomechancis, 1973, vol. 6, pp. 671-680.

A Mathematical Model for the Study of the Mechanics of the Human Vertebral Column, A. Schultz, Journal of Biomechanics, vol. 3, pp. 405-416.

Radiologic Science for Technologists, Third edition, by Stewart C. Bushong, pp. 175-180, 182-211, and 290-303.

Modern Developments in the Principles and Practice of Chiropractic, edited by Scott Haldeman, Chapter 8, pp. 143-170.

X-Cellent X-Ray Company sales brochure for the C-8605 Vertical TV Imaging System.

Medicor sales brochure for the RS-4 Video Fluoroscopic Unit.

York X-Ray, Inc. sales brochure for the Yrk-2001 System.

Peak Performance Technologies, Inc. sales brochures for the Peak 2D Video/Computer Motion Measurement System and the Peak 3d/Video/Computer Motion Measurement Module.

Roentgen Ray Service, Inc. sales brochure for Superline X-Ray Grids.

DIRECTION OF
X-RAY BEAM

METHOD AND APPARATUS FOR COMPARATIVE ANALYSIS OF VIDEOFLUOROSCOPIC JOINT MOTION

BACKGROUND OF THE INVENTION

The invention relates generally to a method and apparatus for the study of the motion of the human body. In particular, the invention relates to a method and apparatus for videofluoroscopic analysis of joint motion which is recorded and compared to a reference recording of previous or desired joint motion.

Since the 1920s, fluoroscopic examinations have been recorded, first on film by a technique known as cineradiography. The ability to record fluoroscopic examinations permitted a means for storage of the exam. This permanent record of the exam could be analyzed at a later date and replayed as many times as necessary at a variety of speeds. The widespread availability of video recording systems in the late 1970s and 1980s has led to the replacement of cineradiography with videofluoroscopy, the process of videotaping a fluoroscopic study for playback on a video cassette recorder. However, there is little use of videofluoroscopy as it relates to the skeletal system. Historically, the primary applications of fluoroscopy have been for study of the gastrointestinal tract, the pulmonary and cardiovascular systems and in myelographic and arthrographic examinations, those systems and studies where organ or fluid movement must be seen if accurate diagnosis is to result. The traditional method of imaging the musculoskeletal system has been, and remains, standard radiographs. The benefits of using fluoroscopy for skeletal analysis has not been widely recognized. Static x-rays simply cannot reveal the same kind of information that dynamic studies provide.

Interest in fluoroscopy has been replaced by interest in computerized imaging techniques. In the 1970s, computed tomography (CT) scanners demanded the radiologists attention, followed by the development of nuclear magnetic resonance (NMR) systems. A new method of skeletal analysis also developed in the 1970s: computer modeling. In this process, the biomechanical functioning of the spine is studied through mathematical analysis, often including model projections, some of which are three-dimensional.

The 1980s have seen a return to interest in fluoroscopy studies. However, the focus of attention now rests on the hook-up of the fluoroscope to the computer, not its hook-up to a video system. Called digital fluoroscopy (or digital radiography or subtraction imaging), this technique subtracts one fluoroscopic image from a later one. The process involves complex computer circuitry and programming and, like CT and NMR scanners, the cost of equipment and complexity of technology limit its availability primarily to hospitals. Thus far, the major application of digital fluoroscopy has been in the study of the cardiovascular system, with bony structures subtracted from the images. Recent developments in medical imaging involve the construction of three-dimensional pictures by computer.

Cine studies of the skeletal system were first reported in the 1950s. This early work was confined to examinations of the cervical spine and consisted primarily of attempts to determine normal and abnormal neck movement. Many reports on the use of cineradiography to study and define joint motion appear in the literature. Numerous joint motion studies using cine have been carried out by doctors of chiropractic. It seems that the chiropractic profession is doing more to fine tune the videofluoroscopic technique than anyone else, partly because chiropractors do not have easy access to other imaging tools such as CTs and NMRs and partly because their profession is more concerned with joint motion, i.e., determining what exactly happens when a joint moves.

James Mertz briefly discussed videofluoroscopic studies of the cervical and lumbar spine (*ACA Journal of Chiropractic*, pages 74–75). Increased ranges of motion most often resulted from injury to the retaining ligaments, while restricted ranges of motion resulted from structural asymmetry, degenerative changes, and muscular imbalances. He observed that stretched ligaments heal by scar formation, but they can no longer maintain relationships of adjacent bone structures; in contrast, muscles may alter the range of motion of bone structures, but they do not affect relationships. Stress patterns (of altered joint motion or relationship) result in joint degeneration; by using videofluoroscopy to evaluate spinal motion, degeneration resulting from hypermobility and hypomobility can be predicted. Although some text books on skeletal disorders point to the usefulness of fluoroscopy, its widespread use as a diagnostic procedure on skeletal disorders is not widely recognized. In general, fluoroscopy is utilized most often for the study of systems other than the musculoskeletal system, primarily the cardiovascular system (i e., angiograms) and the gastrointestinal tract (i.e., upper and lower GI barium studies).

Mintz, et al. (*American Journal of Cardiology*, 1980, 45/2, pages 210–216) discussed an experimental use of videofluoroscopy to study patients undergoing coronary arterial bypass graft surgery. To evaluate left ventricular performance and segmental wall motion, radiopaque tantalum markers were implanted into the left ventricular wall during bypass surgery. Postoperatively, fluoroscopic images were recorded on a video disc recorder and replayed frame by frame. The authors then digitized the images for computer analysis, using a light pen to mark the X and Y coordinates of the implanted marker positions during three successive cardiac cycles. These coordinates were related temporally to the R wave of the analog electrocardiographic signal, recorded as a horizontal bar on the video image. Each measurement was averaged and statistical differences were assessed.

Chiropractors seem to be more involved in the development of the videofluoroscopic technology than other physicians. For example, two research projects, both in Europe, have attempted to measure objectively the motion observed on cineradiographic exams. In general, such projects have employed faulty or weak methodology in trying to elicit objective measurements from moving pictures.

In 1979, Masters and Sugiyama (thesis for Anglo-European College of Chiropractic) reported on the use of cineradiology for measurement of range of movement, roll, and shear of each vertebra between C2–C6. Range of motion was first measured by goniometer and plain films. The cine film was projected onto a screen covered with acetate sheets, where the axes of vertebra were drawn from the projected film for frame-by-frame analysis. They then plotted fourteen different ranges of measurement for each 1/25 of a second onto a graph to detect motions not observable when cine films were run at normal speed. When film was viewed as a moving picture, a fan-like movement of the vertebra was seen. On the other hand, when analyzed frame by frame, graphs indicated that movement really consisted of a ragged see-saw progression as the neck moved. In shear movement, for example, one intersegment appeared to remain static while the rest showed a rocking motion; as the neck moved, another interspace took over this static roll and the previous one rocked on its axis.

Work by Gideon Ariel has focused on computer analysis of biomechanical data and particularly studying athletic performance and making suggestions for improvements. His method involved filming athletes participating in throwing events by high-speed motion picture camera set at a 90° angle to the athlete's sagittal plane. After being projected upon a translucent glass screen, the film was digitized with a sonic stylus, and the X and Y coordinates were stored in a computer's memory. As each frame was digitized, joint centers were projected onto a graphic display screen and connected by lines to form stick figures. Computer analysis calculated parameters such as total body center of gravity, segment velocities and accelerations, joint forces and movements of force.

Two other types of fluoroscopic imaging are known. Dynamic radiography, developed in 1974, is a noninvasive technique utilizing scatter radiation rather than direct transmitted radiation to monitor and measure myocardial mechanics during fluoroscopy. Another technique relates to the photokymograph (PKG), a noninvasive instrument for recording segmental myocardial wall motion from self-illuminated images, such as those produced by fluoroscopy, cine ventriculography, two dimensional sonography, and scintigraphy. As with all the other prior art discussed above, these fluoroscopic imaging techniques are unable to provide an objective comparative analysis of joint motion.

SUMMARY OF THE INVENTION

It is an object of this invention to provide an apparatus for analyzing the flexure of a joint between first and second bones resulting from the movement of the bones.

It is another object of this invention to provide an apparatus which permits the videofluoroscopic analysis and comparison of joint motion.

It is another object of this invention to provide a videofluoroscopic system which generates clear, accurate video images of bone and joint motion thereby permitting a means for recording images in order to conduct detailed analysis and comparison of patterns of the motion.

It is yet another object of this invention to provide a videofluoroscopic system which permits the objective comparison of present and reference representations of joint motion.

It is yet another object of this invention to provide a videofluoroscopic system which permits the comparison of joint motion to determine whether the joint motion follows normal patterns and is within normal limits or beyond preset limits indicating an alarm condition.

It is a further object of this invention to provide a digital videofluoroscopic joint motion comparative analysis system.

It is another object of this invention to provide a videofluoroscopic system which objectively permits the determination of minimum and maximum angles of motion of joints and bones which form joints.

It is another object of this invention to provide an apparatus for immobilizing a lower torso, thereby permitting standardized videofluoroscopic analysis of the lumbar spine, and to provide a videofluoroscopic system which produces accurate images resulting from such analysis.

It is another object of this invention to provide a method for analyzing the flexure of a joint between first and second bones resulting from movement of the bones.

It is yet another object of this invention to provide a method for permitting the objective comparison of a reference or desired representation with a present representation of joint motion.

It is yet another object of this invention to provide a method for generating videofluoroscopic images of the lumbar spine which are clear and accurate and which may be used in comparative lumbar spine analysis.

It is an object of this invention to provide a system which combines both videofluoroscopy and computer analysis, especially in a way to permit objective interpretation of an examination.

It is another object of this invention to provide a videofluoroscopic examination system which, by computer analysis, determines normal and/or abnormal ranges and patterns of motion, leading to the diagnosis of conditions based on the objective measurements obtained.

It is another object of this invention to provide a system which would permit standardized interpretation of skeletal fluoroscopic studies.

The invention comprises an apparatus for analyzing the flexure of a joint between first and second bones resulting from movement of the bones. In one form, means creates at least two successive video images of the movement of the bones and the resulting flexure of the joint. Means compares the successive video images to a reference representation corresponding to a desired or previous movement of the first bone with respect to the second bone and the resulting flexure of the joint.

In another form, means creates at least two successive video images of the movement of the bones and the corresponding flexing of the joint. Means identifies a reference point on the first bone in each video image and a monitoring point on the second bone in each video image. Means generates a present representation corresponding to the movement of the monitoring points with respect to the reference points.

In another form, means evaluates at least two successive video reference images of the movement of the bones and the resulting flexure of the joint and generates a reference representation corresponding thereto. Means evaluates at least two successive video present images of the movement of the bones and the resulting flexure of the joint and generates a present representation corresponding thereto. Means compares the reference representation to the present representation.

In another form the invention comprises a fluoroscopic system. Means provides radiation toward an object to be evaluated. Means, located adjacent a side of the object opposite the providing means, intensifies the provided radiation and generates an image of the object therefrom. A crisscrossed grid is located between the intensifying means and the object to enhance the image of the object generated by the intensifying means.

The invention also comprises a method for analyzing the flexure of a joint between first and second bones resulting from movement of the bones comprising the steps of creating at least two successive video images of the movement of the bones and the resulting flexure of the joint; and comparing the successive video images to a reference representation corresponding to a desired or previous movement of the first bone with respect the second bone and the resulting flexure of the joint.

In another form the method comprises the steps of creating at least two successive video images of the movement of the bones and the corresponding flexing of the joint; identifying a reference point on the first bone in each video image and a monitoring point on the second bone in each video image; and generating present representation corresponding to the movement of the monitoring point with respect to the reference point.

In another form the method comprises the steps of evaluating at least two successive video reference images of the movement of the bones and the resulting flexure of the joint; generating a reference representation corresponding to the evaluated reference images; evaluating at least two successive video present images of the movement of the bones and the resulting flexure of the joint; generating a present representation corresponding to the evaluated present images; and comparing the reference representation to the present representation.

In another form, the invention comprises a fluoroscopic method including the steps of providing radiation toward an object to be evaluated; intensifying, by using an intensifier located adjacent a side of the object opposite the provided radiation, the provided radiation; generating an image of the object therefrom; and placing a crisscrossed grid located between the intensifier and the object adapted to enhance the image of the object generated by the intensifier.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE INVENTION

Figure 1:
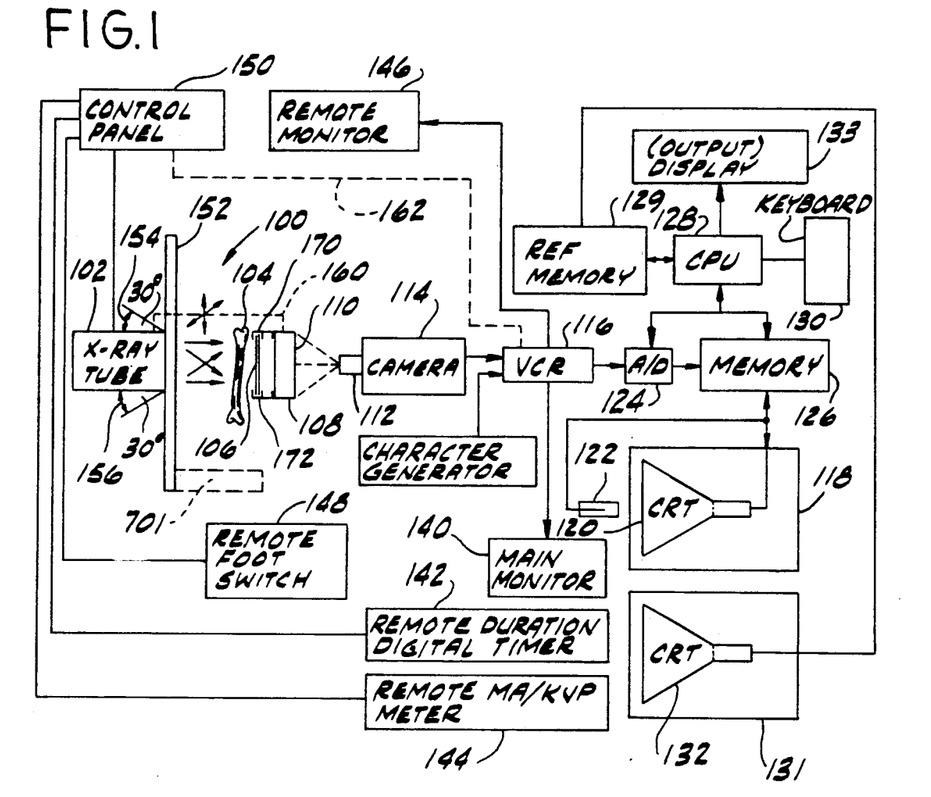
FIG. 1 is a block diagram of an apparatus for comparative analysis of videofluoroscopic joint motion according to the invention.

Referring to FIG. 1, reference character 100 generally refers to a fluoroscopic system including x-ray tube 102 for providing radiation toward a subject 104 such as an object, bone or limb to be evaluated. Subject 104 absorbs and/or reflects radiation which impinges upon it so that only radiation which passes around and/or through the subject strikes grid 106 to pass through grid 106 and strike image intensifier 108 which is preferably a 9-6 dual field image intensifier tube. The radiation level is adjusted, depending on the density of the subject, by adjusting the controls on control panel 150 so that some radiation will pass through and around subject 104 and through grid 106 to strike image intensifier 108. The result is that image intensifier converts the radiation which strikes it into visible light so that screen 110 of image intensifier 108 provides a visual image corresponding to subject 104. The visual image will vary in intensity in accordance with the density of the various portions of subject 104 which are irradiated.

The image on screen 110 of intensifier 108 is photographed by lens 112 of video camera 114 and converted into an analog signal which is stored in an analog storage device such as video cassette recorder (VCR) 116. Video monitor 140 includes a cathode ray tube (not shown) for displaying video images being stored in VCR 116.

Figures 2, 3:
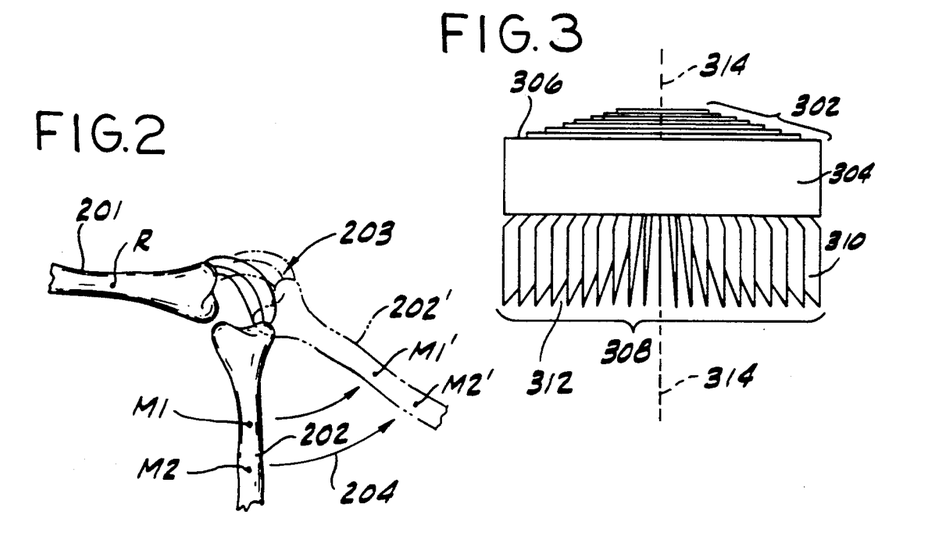
FIG. 2 is a diagrammatic sketch illustrating the movement of two bones.
FIG. 3 is a perspective view of a criss-crossed grid used in combination with the image intensifier of a fluoroscope to enhance the image.

In one form, the invention as illustrated in FIG. 1 constitutes an apparatus for analyzing the flexure of a joint between first and second bones resulting from movement of the bones as shown for example in FIG. 2. A first bone 201 may be connected to a second bone 202 by a joint 203 comprised of ligaments, tendons, cartilage and/or other interconnecting tissues. The first bone 201 may be immobilized by strapping it to table 152 so that the second bone 202 moves with respect to the first bone 201 to position 202' as indicated by arrow 204. In order to analyze the motion of bone 201 with respect to bone 202 and the resulting flexure of joint 203, bones 201 and 202 joined by joint 203 would be placed within fluoroscopic system 100 in the position as indicated by subject 104. When the joint 203 is then flexed, it is seen in a series of video images on the screen 110 of intensifier 108 of the bones as they move. This image would be recorded by camera 114, stored on tape by VCR 116 and displayed on monitor 140. Character generator 117 may be used to provide character data to VCR 116 to label the images. In addition, a time base corrector may be used to correlate image timing of slow motion and still frames.

In particular, as the patient moves bones 201 and 202, successive video images would be created on screen 110 showing the movement of these bones. Referring again to FIG. 1, X-ray tube 102 and intensifier 110 are mechanically connected together as indicated by reference character 160 and are suspended or otherwise supported for simultaneous horizontal and/or vertical movement with respect to table 152. As the patient moves the bones being fluoroscoped, the operator moves tube 102 and intensifier 110 simultaneously therewith so the joint or area being evaluated is maintained within the beam of the fluoroscope to create successive video images of the moving bone which are detected by camera 114 and stored in VCR 116. Assuming that VCR 116 employs a standard NTSC format, 30 frames per second would be stored in VCR 116 so that 30 images per second would be generated by the movement of the bones. Each of these frames may be converted into digital information by analog-to-digital (A/D) converter 124 and stored in memory 126. CPU 128 would control the timing and operation of A/D converter 124 and memory 126. Alternatively, CPU 128, instructed by an operator through keyboard 130, converts and stores only selected video images.

Additionally, still video images of the bones, such as illuminated static x-rays (i.e., plain films) of the bones, may be detected by camera 114. These still images may be placed at the beginning or end or interlaced with successive video images for visual comparison by an operator viewing the images or by analysis by CPU 128. As noted above, character generator 117 may be used to label the recorded images.

X-ray tube 102 is provided with a remote timer 142 placed on or near the monitors so that the operator can keep track of the duration of exposure and of the time which is elapsing during the movement of the bones. Timer 142 is a clock which operates as long as x-ray tube 102 is providing radiation to irradiate subject 104. A remote meter 144 such as a milliampere (MA) meter and/or a kilovolts peak (kVp) voltmeter may also be provided adjacent to monitor 140 so that the operator can simultaneously monitor the intensity level of the radiation being provided by x-ray tube 102. The remote meter 144 provides the operator with an indication of the current (or voltage) being used to generate radiation from tube 102 for irradiating the subject 104. With this arrangement, the operator is able to simultaneously monitor the intensity and time of exposure of the subject and move the tube and intensifier simultaneously with subject movement while viewing the actual images that are being recorded on monitor 140. The operator controls activation of the fluoroscope by remote foot switch 148. Also, a technician may be at the control panel 150 to assist the operator and a remote monitor 162 may be located adjacent the control panel 150 to permit the technician to view the images being recorded.

Timer 142 can be added to pre-existing x-ray control panels 150. Many doctors, hospitals and clinics have pre-existing equipment and would require, as part of this invention, digital timer 142 that can be purchased as an accessory to be added to the pre-existing equipment. The digital time 142 is a special clock attached and wired to the x-ray tube control panel 150. Its dimensions are approximately 4"×4"×2", with numerals large enough to be seen from across a room and illuminated so they can be seen in the dark. When reset, the timer always begins at the time 0:00. It is activated by the remote foot switch 148 (or a toggle switch located on the control panel 150) that activates the x-ray tube 102. Whenever the operator signals the x-ray generator to activate the tube to generate the x-ray beam, the digital timer 142 is simultaneously activated. Conversely, the timer stops when the beam is not being emitted; for example, it is deactivated between views. Therefore, the timer displays cumulative x-ray exposure. By pushing a reset button, the operator resets the timer to 0:00 for each different fluoroscopic exam.

The purpose of the digital timer 142 is to give the exact time, in minutes and seconds, of the total exposure of x-ray beam's emission during a fluoroscopy exam. Duration of exposure is important in any radiographic/fluoroscopic procedure. Along with measuring exact exposure time, the digital timer 142 also provides a record of the passage of real time during the procedure, thereby documenting the actual time elapsed.

Remote television monitor 146 is another add-on accessory not included in fluoroscopy systems. Monitor 146 is mounted on or near the x-ray control panel. This remote monitor may be a standard 5" screen, black-and-white television that is synchronized with the main TV monitor. The doctor conducting the fluoroscopic exam views the procedure on the main monitor 140. The purpose of the remote monitor 146 is to provide a way for an assistant to monitor the same field of view as that seen by the doctor, even though the assistant is standing near the control panel, often in another part of the room. The assistant can therefore see and evaluate the image quality and make adjustments in kVp and mA settings that are necessary for image enhancement. Milliampere Seconds (mAs) is a measure of the current per time, i.e., the number of electrons generated per second. The mAs measurement determines the density (film blackness) of the image.

Kilovolts peak (kVp) is a measure of the peak voltage applied to the x-ray tube and is responsible for the speed of the electrons and therefore determines the "strength" of emitted x-rays (their ability to penetrate the body). Differing kVp settings alter the image's contrast (gray scale). Such adjustments are made at the control panel, which means the doctor often cannot reset the kVp and mAs dials because he/she is conducting the exam and operating other equipment. The assistant's ability to see the procedure on a remote TV monitor is not essential, but it can improve the quality of the image recorded on the videotape.

The main monitor 140—a 19" black-and-white television with 750 lines of horizontal resolution—is encased and bolted to a movable cart, which can be wheeled to any position to accommodate the doctor's ease of view. The TV monitor is housed in a metal casing, surrounded on all sides except for the screen side. The videocassette recorder 116 is mounted on top of the casing of TV monitor 140 in a metal "sleeve". Other shelves/openings for additional equipment can be mounted on top of the VCR. These equipment casings are based on the same principle as rack-mounted sound systems. Such a system stabilizes and secures both the TV and the VCR so they cannot fall or slide when the cart is moved.

Monitor 140 (and remote monitor 146) may be connected to control panel 150 to display a digital clock in a corner of its screen which shows the real time elapsing during the fluoroscopic exam. In another corner of the screen, a reference point is shown, to be used later in the computer analysis of joint movement. (This reference point provides a consistent standard against which to measure angles.) Since the videotape records everything appearing on the TV monitor screen, both time and space are permanently, relatively documented as part of the exam.

Another add-on accessory that increases the convenience of this invention and enhances image quality is remote mA meter 144 bolted to the side of the main TV monitor casing. This is an illuminated mA meter, adapted to serve as a remote unit. With a remote meter, the doctor conducting the exam can easily see the mA setting because the meter is lighted and attached to the TV monitor; without such a remote unit, only the assistant standing at the control panel can see the mA setting, which fluctuates as the automatic brightness stabilizer adjusts the level of image brightness. A remote meter measuring kVp settings can also be attached to the TV monitor. Both mA and kVp settings influence image quality and determine radiation exposure to the patient. It is therefore important for the doctor to know these levels during the examination procedure.

The fluoroscopy system of the invention also includes crisscross grid 106 as a necessary component used during the examination procedure. When thick body parts (such as the lumbar spine area) are x-rayed, more scatter radiation reaches the film. Scatter radiation causes graying of densities, producing a fog-like effect and resulting in decreased image clarity of bony structures. The purpose of the grid 106 is to absorb and/or redirect some of the scatter radiation and better focus the primary (undiverted) x-ray beam for a higher contrast picture. In other words, a grid cleans up scatter radiation and selectively directs these multi-directional rays so they are more constructive. To use the grid 106, a higher kVp must be used in order to strengthen the x-ray beam's ability to penetrate because of grid absorption. However, the improvement in image quality compensates for this increased exposure; without a grid, the image's contrast is lost in the fog left by scatter radiation.

The crisscross (or cross-hatch) grid 106 is the preferred type of grid to be incorporated into this system, although linear parallel and linear focused grids may also be used. The grid 106, as illustrated in FIG. 3, consists of crossed sections of radiopaque material such as lead foil strips 310, which act as x-ray absorbers, and aluminum foil interspacers 302 or other radiolucent material between the lead strips. A crisscross grid is actually two grids, one above the other, with the lead strips of one grid perpendicular to the lead strips of the other. When placed together in a frame, the two become a crossed grid. Grid ratio refers to the height of the lead strips compared to the space between strips. A higher grid ratio results in more clean up of scatter radiation (since more rays are absorbed and focused). For fluoroscopic studies of thick body parts, a crisscross grid ratio should be at least 8:1/8:1 (8:1 for both the vertical and horizontal grids crossed in the frame) and may be as high as 16:1/16:1. For studies that require angled tilting of the x-ray tube, a linear grid having a ratio of at least 12:1 is needed.

The grid 106 is positioned in front of the image intensifier 110, mounted either on the spot-film tower or directly on the image intensifier itself. Many fluoroscopy systems do not include a spot-film tower. If there is no tower, a circular grid can be mounted directly onto the input phosphor end of the image intensifier. The grids should be easily interchangeable. For example, a system wherein grids are mounted on tracks (similar to the design for tower mounting) may be used. A cross-hatch or a linear grid could then be slid into position as needed.

The x-ray beam passes from the x-ray tube, through the patient, then through the grid, where the beam is picked up by the image intensifier and converted to light. In the system of the invention, the input phosphor end of the image intensifier can be slipped into a special mounting on the back of the spot-film tower, which is attached to the x-ray table. The image intensifier is thereby anchored to the tower. By sliding the tower along a system of tracks, it can be moved from the foot of the table to the head. The "face" of the tower is approximately 40" from and parallel to the table surface; an arm, perpendicular to the table and tower faces, joins the two. A double set of metal parallel tracks are mounted onto the face of the image intensifier 110, as shown in FIG. 1, or onto the face of the spot-film tower—one set directly inside the other—so the square grids can be slid into position and/or interchanged. One set of grid-mounting tracks holds a linear grid (not shown), while another track holds cross-hatch grid 106. The operator therefore has the option of using no grid, a linear grid, or the crossed grid, depending on the part of the body being filmed. This sliding grid system allows for quick and easy interchanging of grids; they are permanent, yet movable.

This system for conducting a videofluoroscopic examination includes an x-ray table 152 with an up and down tilting x-ray tube 102 housed inside. The x-ray tube is the apparatus which emits the x-rays and directs the beam toward the patient. The surface of the table 152 is kept parallel to the floor for fluoroscopy studies which require the patient to lie down. It can be tilted 90° to an upright position (perpendicular to the floor) for weight-bearing studies which require the patient to stand. Whether the patient 104 is lying or standing, he/she is positioned between the x-ray table that houses the x-ray tube and the image intensifier.

In addition to the tilting table, the x-ray tube within the table also tilts with respect to the table as indicated by arrows 154, 156. Tube tilt is desirable for x-ray studies of the spine; it is responsible, in part, for the superior pictures which can be obtained by the invention. In order to clearly image a joint, the x-ray beam must pass through the same plane as the joint surface (otherwise, portions of the joint are obscured by intervening anatomical structures). To accommodate the angled planes of some joints, the x-ray beam must be similarly angled. "Tube tilt" refers to the angulation of the tube in relation to the head (cephalad) or foot (caudad). A tube can tilt within a vertical plane from 0°-30° cephalacally (toward the patient's head) as indicated by arrow 154, or from 0°-30° caudally (toward the foot) as indicated by arrow 156, yielding a total capability of rotating in a 60° arc. The angles of tube tilt are the same regardless of the table's position. The amount of rotation, or tilt, desired depends upon the amount of angulation from the flat plane of the joint being visualized. Using a toggle switch, the operator can automatically tilt the tube to the desired angle. When tilting the tube, it is preferable to use a parallel grid which is parallel to the direction of tilt of the tube.

A representation, as used herein, includes a set of data which identifies the movement or patterns of movement of a bone or the flexure of a joint between first and second bones resulting from movement of the bones forming the joint. The successive video images corresponding to bone movement or joint flexion are one form of a present representation which would then be compared to a reference representation stored in reference memory 129. The reference representation corresponds to a desired or previous movement. The representations may be compared directly to each other, or may be further analyzed.

The present representation images would be evaluated in the following manner which relates to joint flexion and is equally applicable to evaluation of bone movement, in general. A first video image of the two bones and joint is displayed on CRT 120 of monitor 118. This can be accomplished by CPU 128 automatically dumping the image information from memory 126 into monitor 118 or CPU 128 can be instructed via keyboard 130 to load a particular first video image for analysis. As best shown in FIG. 2, a reference point R is then selected on first bone 201. This point can be selected by the operator by using light pen 122 to close a feedback loop indicating the point on bone 201 as displayed by CRT 120 which will function as the reference point. Reference point R should be a stationary point with respect to the joint being evaluated. Alternatively, CPU 128 may evaluate the image of bone 201 and, based on the varying intensities of the points which define the image of bone 201, select a unique location on the image of bone 201 as the reference point. Similarly, a monitoring point Mi remote from point R is selected on bone 202.

As noted above, bone 201 would preferably be immobilized so that the successive images would effectively be images of the movement of the bone 202 while bone 201 remains in a fixed position. As a result, bone 201 and reference point R would be essentially in the same location with regard to successive images. It is contemplated that the invention may be used for three-dimensional evaluation and analysis as well as the two-dimensional approach described herein. The third dimension may be projected by a computer program or several angles of the subject can be fluoroscoped and superimposed to generate three-dimensional information.

Preferably reference point R would be a point on bone 201 which could be readily identified on each image. For example, it may be a spur or indentation on the bone which is readily apparent in each successive image. Alternatively, the operator could manually measure a set distance from the end of the bone to uniformly select the point R on each successive video image of bone 201.

The coordinates of monitoring point M1 with respect to reference point R are then determined either by the operator visually analyzing the image on the face of CRT 120 (such as by measurement thereof) or by analysis of the CPU 128. These coordinates are stored in memory 126.

The evaluation process is then repeated for each succeeding video image of the present representation. After all the video images of the present representation have been evaluated as indicated above, a series of coordinates corresponding to the movement of the monitoring point from point M1 to point M1' have now been stored in memory 126.

The present representation would then be compared to a reference representation. This comparison may be performed visually by the operator or automatically by CPU 128. The reference representation is derived from a reference series of successive video images of a desired or previous movement. The reference series is evaluated in the same way the succeeding video images of the present representation are evaluated as noted above. Alternatively, the reference representation may be an empirical formula or representation derived from analysis of various images.

In one form, the visually comparison of the present and reference representations involves direct comparison of the video images of the reference and present representations. The operator would instruct CPU 128 through keyboard 130 so that the successive video images corresponding to the reference and present representations may be simultaneously viewed. CPU 128 would display the first successive video image of the present representation stored in memory 126 on CRT 120 of monitor 118 and simultaneously display the first successive video image of the reference representation stored in reference memory 129 on CRT 132 of reference monitor 131. A doctor or other qualified professional would then compare the images on CRT 120 to the images on CRT 132. Each succeeding video image of the present representation would then be displayed on monitor 118 and the next video image of the reference representation would then be displayed on reference monitor 131. For each image, the professional would visually compare the images. This process would continue until each selected video image of the present representation to be analyzed has been compared to a corresponding video image of the reference representation.

In another form, the visual comparison is accomplished as follows. An operator instructs the CPU 128 to provide via display 133 the coordinates corresponding to the reference and present monitoring point movement. The operator would then calculate (or estimate) equations defining a mathematical representation of the path of movement corresponding to the reference monitoring point movement and the present monitoring point movement. The coordinates and/or curves are then compared by a professional.

The automatic comparison of the reference and present representations is performed by CPU 128. CPU 128 would calculate the equations corresponding to the reference and present monitoring point movement and compare the equations as indicated below. Alternatively, the reference and present images can be superimposed onto each other for viewing and comparative analysis by a professional.

In order to provide an accurate comparative analysis of the flexure of the joint and the corresponding bone motion, it is necessary that a well defined image be generated by the screen 110 of intensifier 108. Generally, the radiation emitted by x-ray tube 102 and impinging upon intensifier 108 is not parallel. Therefore, even well defined subjects which are fluoroscoped will result in images provided on screen 110 which are not well defined. This is due to the fringing effect of the non-parallel radiation and the scattering of the radiation which passes over and around the subject 104. When larger subjects are being fluoroscoped, such as when lumbar spine motion studies are being made, the intensity of the radiation emitted by x-ray tube 102 must be significantly increased to ensure adequate penetration of the portion of the body being fluoroscoped, further increasing the fringing effect.

The technologist operating fluoroscope 100 from control panel 150 has the option of increasing the current (milliamperes) or the peak voltage used to generate the radiation. Increasing the milliamperes usually generates enough radiation to provide a satisfactory image on the intensifier, but may result in an unacceptably high patient dose. On the other hand, a much smaller increase in the voltage is usually sufficient to provide adequate fluoroscopic radiation and this can be done at a much lower patient dose. Unfortunately, when the voltage is increased, the level of scatter radiation also increases and therefore the image contrast decreases. Accordingly, crisscrossed grid 106 should be employed between subject 104 and intensifier 108 to reduce the level of scatter radiation arriving at the intensifier. This crisscrossed grid 106 is illustrated in FIG. 3. Grid 106 is an extremely effective device for reducing the level of scatter radiation. It is an array 302 of elongated planar members 304 of radiopaque material alternating with sections of radiolucent (interspace) material 306. This array 302 is perpendicular to and immediately over another array 308 of elongate planar members 310 of radiopaque material alternating with sections of radiolucent (interspace) material 312. Grid 106 is designed to transmit only those x-rays whose direction is on a line substantially parallel to axis 314 from the source to the intensifier. X-rays that travel obliquely (at an angle) are absorbed in the radiopaque material. It has been found that a crisscrossed grid having a ratio in the range of from 8:1 to 10:1 is most effective for fluoroscopic analysis of dense subjects.

Figure 4:
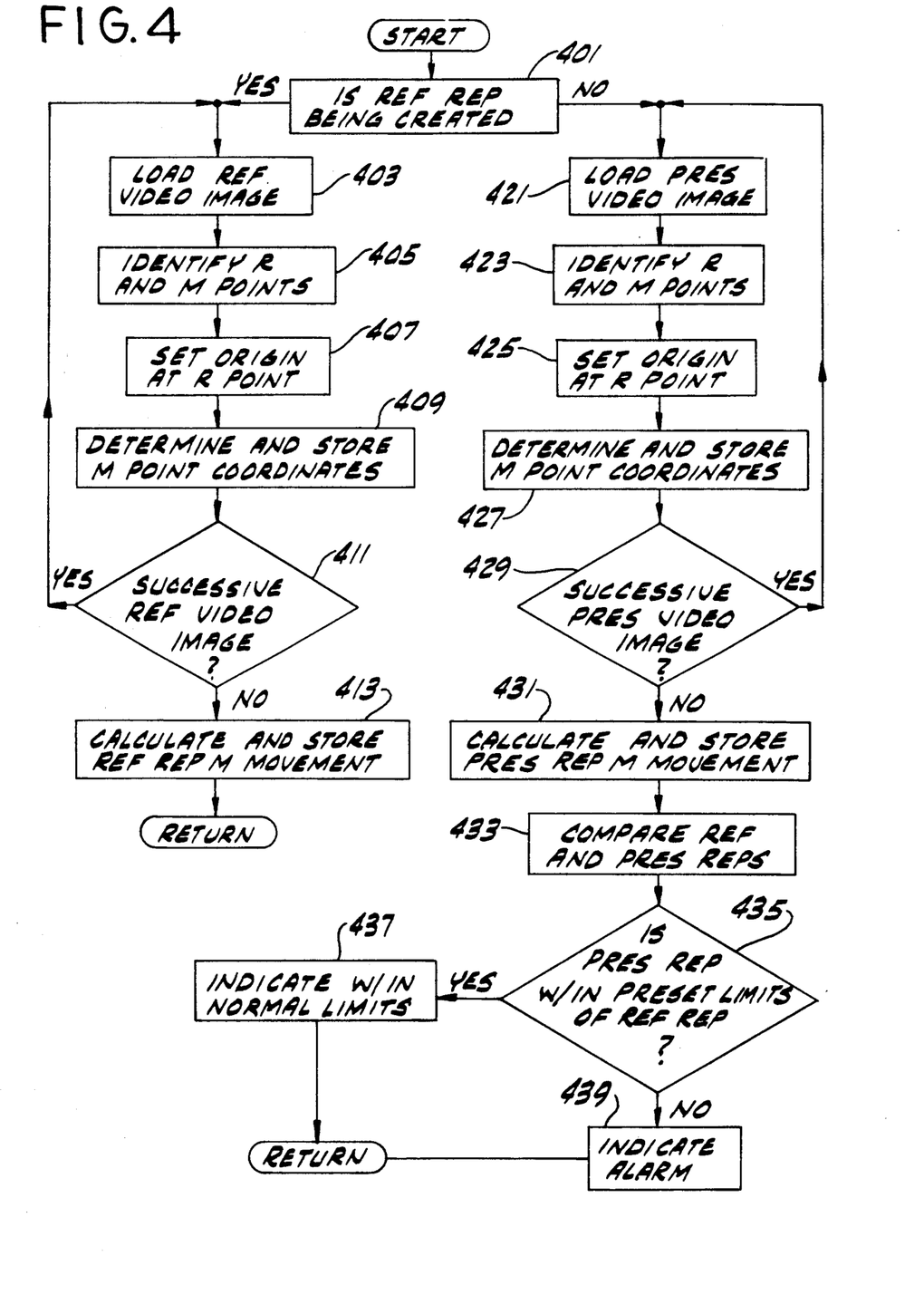
FIG. 4 is a flowchart illustrating the method for comparative analysis of fluoroscopic images of joint motion according to the invention.

Referring to FIG. 4, a method for evaluation and comparative analysis of videofluoroscopic joint motion is illustrated in flowchart form. Initial step 401 requires a determination as to whether reference representation images or present representation images are being evaluated. In the event that reference representation images are being evaluated, the process proceeds to steps 403–413 where each reference video image is evaluated. The image to be evaluated is loaded into memory 126 by step 403 and then displayed on the screen of CRT 120. (The image may also be stored in reference memory 129 for visual comparison). At step 405, the operator visually (by using light pen 122) or the CPU 128 automatically (by selecting a point of unique contrast and/or intensity) identifies the reference point R on the immobilized bone in the image and identifies the monitoring points M on the moving bone. At step 407, the origin of the coordinate system to be used is set at the reference point R. The operator or CPU 128 then determines at step 409 the coordinates of the monitoring points M and stores those coordinates in reference memory 129. Step 411 is a decision step to determine whether successive reference video images are to be evaluated. At least two references images must be evaluated. After each of the reference images has been evaluated by steps 403–409, the process proceeds to step 413 wherein CPU 128 calculates the reference representation, i.e., an equation representing the monitoring points M movement on the various successive reference images that have been evaluated. This reference representation is then stored in memory 129.

In the event that present representation images are being evaluated, the evaluation process begins with step 421 wherein the first present video image is loaded into memory 126 and displayed on the screen of CRT 120. At step 423, the operator or CPU 128 identifies the reference point R on the immobilized bone in the image and identifies the monitoring points M on the moving bone. Thereafter, the origin of the coordinate system to be used is set at the reference point by step 425. At step 427, the operator or CPU 128 determines the coordinates of the monitoring points M and those coordinates are stored in memory 126. At decision step 429, a determination is made as to whether successive present video images are to be evaluated. At least two present images must be evaluated. When all the present video images have been evaluated in accordance with steps 421–427, CPU 128 performs step 431 to calculate the present representation, i.e., an equation representing the movement of monitoring points M and to store that present representation in memory 126.

At step 433, CPU 128 then compares the reference representation to the present representation which, as noted above, may be patterns of movement as well as individual representations of movement. Decision step 435 then determines actual measurements of the motion (such as angles and lines of movement), whether the present representation is within preset limits of the reference representation, and/or whether the patterns of movement of the present representation are consistent with the patterns of movement of the reference representation. These preset limits may be stored in reference memory 129, memory 126 or may be entered by the operator into CPU 128 via keyboard 130. If the present representation is within the preset limits, the evaluation proceeds to step 437 wherein CPU 128 indicates that the present representation is within normal limits. This indication may be made on display 133 or printed on a printer or other output means. Alternatively, if the present representation is not within the preset limits of the reference representation, an alarm is indicated by CPU 128 at step 439 to advise the operator of this condition.

Figure 5:
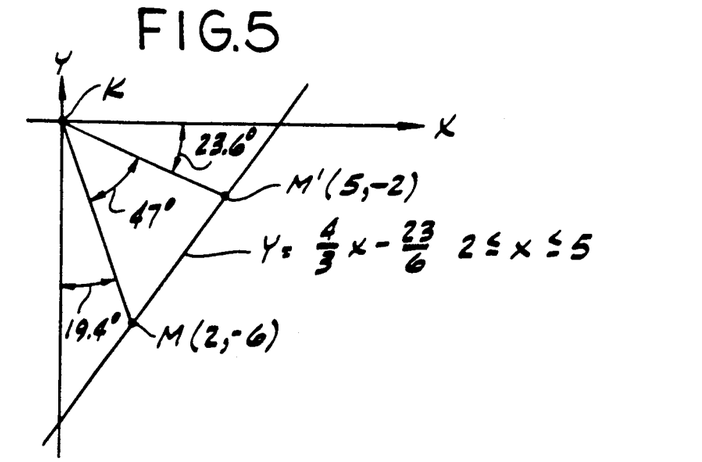
FIGS. 5 and 6 illustrate reference and present graphs, respectively, for analyzing the movement of monitoring points with respect to reference points according to the invention.

A simplified example of the process according to the invention will be explained with reference to FIGS. 5 and 6. FIG. 5 shows a Cartesian coordinate graph on an XY axis for two reference representation images having reference point R and monitoring point M on the first video image and monitoring point M' on the second video image. Monitoring points M and M' correspond to the desired minimum and maximum, respectively, flexure of the joint. The coordinates of point M are (2, −6) and the coordinates of M' are (5, −2). Therefore, the reference representation has a pattern of motion represented by the following equation for motion from point M to point M':

$$Y = (4/3)X - 26/3, \text{ for } 2 \leq X \leq 5 \quad (1)$$

Figures 6, 7:
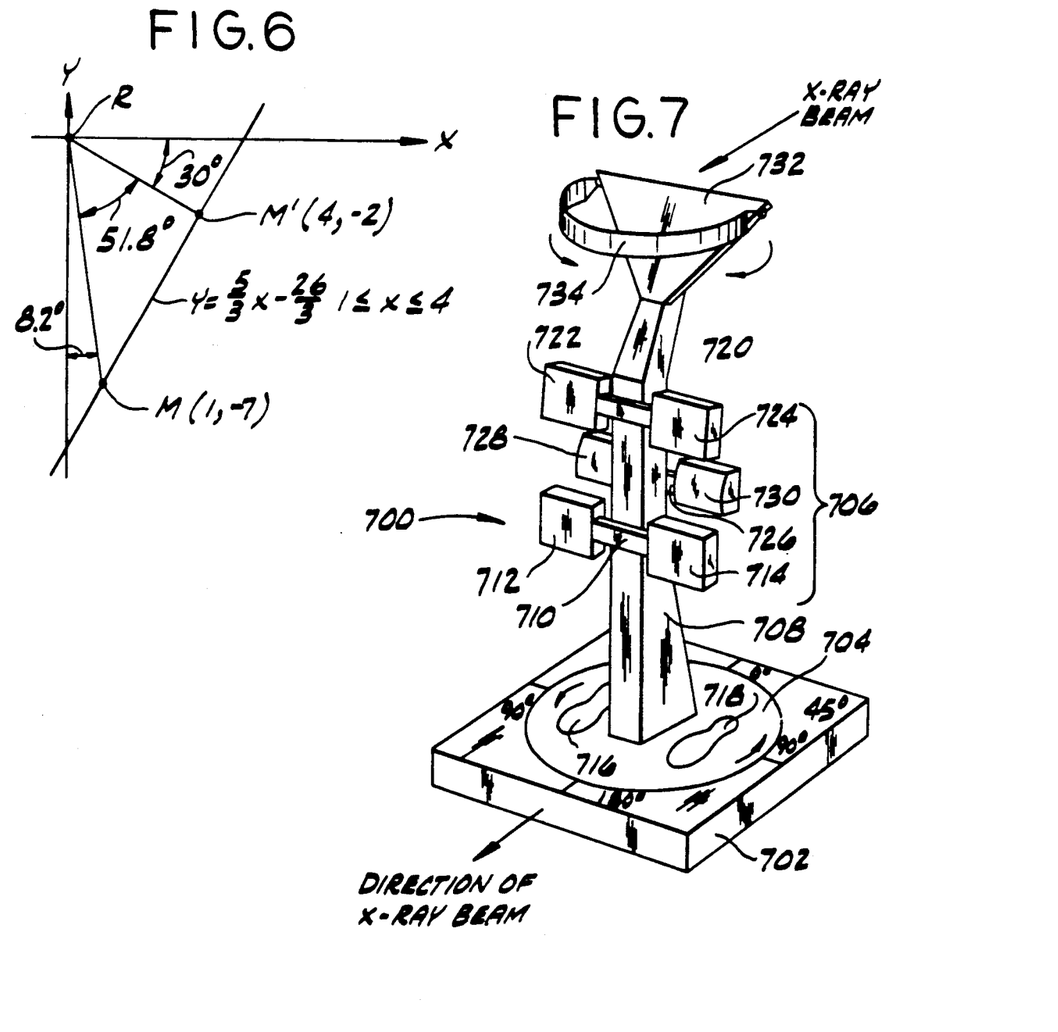
FIG. 7 illustrates a structure according to the invention for immobilizing the legs to permit a lumbar spine motion study.

In contrast, FIG. 6 illustrates an XY coordinate graph for two present representation images of motion of the same joint from point M having coordinates (1, −7) to point M' having coordinates (4, −2). Therefore, the present representation has a pattern of motion represented by the following equation for motion from point M to point M': of:

$$Y = (5/3)X - 26/3, \text{ for } 1 \leq X \leq 4 \quad (2)$$

Upon comparing equations 1 and 2, the following information can be determined. In the reference representation, illustrated by FIG. 5 and resulting in equation (1), the joint had a range of motion of 47°. On the other hand, in the present representation, illustrated by FIG. 6 and resulting in equation (2), the joint had a range of motion of 51.8° suggesting a hyperextension of the joint. The lowermost range of motion (corresponding to M in FIG. 6) increased suggesting that the hyperextension may have occurred at that point whereas the uppermost range of motion (corresponding to M' of FIG. 6) decreased indicating hypoextension of the joint at that point. The slope of the motion represented by the line of equation 1 is 4/3 whereas the slope of the motion represented by the line of equation (2) is 5/3 further indicating a change in the mobility of the joint being evaluated and compared. These factors are then compared by an operator or the CPU to preset limits to determine whether or not the joint motion of the present representation images as illustrated in FIG. 6 is within normal limits. When more than two monitoring points M are used to determine a reference representation or a present representation, the equations then take the form of a polynomial because the motion of the joint will generally be in a curvilinear path.

It is contemplated that a more sophisticated analysis of the monitoring points with respect to the reference point may be used. For example, the relative angular movement of the points may be measured; the specific shapes of the path of movement of the points may be individually or collectively compared or superimposed; the velocity, acceleration or deceleration of movement of each point along the path may be compared; any of the above-mentioned parameters may be compared to a reference, to another point or to a previous measurement in both two-dimensional and three-dimensional configurations: various reference points could be selected and the monitoring points could be compared with respect to each of the reference points; or a polar coordinate system or other coordinate system may be used for comparative analysis in place of a Cartesian coordinate system.

An important part of this system is stabilizing platform 700. This metal device, having a base 702 with a surface area of approximately 3'×2', clamps onto the foot of the x-ray table (see FIG. 1) and is braced with supports (not shown) to remain securely perpendicular to the table. Alternatively, this device may be freestanding. This device is removable and attached to the table when weight-bearing studies of the lumbar and cervical spines are conducted. After it is attached, the table is tilted to its upright position; the patient then stands on the device, which is now parallel to the floor. A circular platform 704 is centered in this surrounding rectangular device. This circular platform 704 may be motorized to rotate to different, preset positions: 180° opposite from the x-ray beam, 90° and 45° to both the right and left of the x-ray beam's path. By remote control, the doctor conducting the study can automatically move the circular platform—and the patient standing upon it—to the desired preset position. This device ensures that the patient is always positioned at an exact angle (for example, 90° to the right of the x-ray beam, not 78°).

Rising upright from the platform base (and therefore perpendicular to it) is a system of restraints 706 that brace and stabilize the patient's lower body. This part of the device secures the patient's knees, thighs, and pelvis so they are gently but firmly immobilized. The spine is left free to move so the patient can rotate his upper body and bend laterally, forward, and backward (flexion and extension). Because the restraints immobilize the lower extremities, the patient cannot move too far or step out of the fluoroscope's field of view. This confines spinal motion to the spine only and avoids influence by movement of the lower body.

Platform 704 permits the standardization of the videofluoroscopic study of spinal motion. It ensures that movement can occur only in the spine and only at specific angled positions relative to the x-ray beam. Such standardization enhances the chance that fluoroscopic study of the spine will consistently be the same; the exam is therefore reliable and repeatable, even when performed at different times and by different examiners. Since part of this system involves computer analysis of spinal motion, a consistent procedure for obtaining the videotapes of moving anatomy is a necessity. Without it, clear reference points cannot be guaranteed and computer analysis will be compromised.

Stabilizing platform 700 is for immobilizing the lower body so that a lumbar spine motion study may be conducted. When such a study is conducted, the legs and pelvis are generally immobilized and the subject flexes the spine while the spine is under videofluoroscopic examination. Base 702 is a generally planar, rigid material which supports platform 704 for rotation about an axis substantially perpendicular to the plane defined by base 702. Base 702 has a recess therein for platform 704 to permit axial rotation thereof. The base may include bearings (not shown) between the base and the platform to reduce rotational friction therebetween. Accordingly, base 704 constitutes means for rotating the platform about the axis. Platform 704 perpendicularly, axially supports vertical support post 708. Right and left footprint-shaped indentations 716, 718 may be located on platform 704 to assist the subject in locating the position of the feet. Lower horizontal support bar 710 is rigidly, perpendicularly mounted to vertical support post 708. The ends of bar 710 terminate in right and left pads 712 and 714, respectively, for restraining the front of the legs of the subject immediately below the knee. Upper horizontal support post 720 is rigidly, perpendicularly mounted to vertical post 708. Each end of bar 720 terminates in right and left pads 722 and 724, respectively, for restraining the front of the legs of the subject immediately above the knee.

Intermediate horizontal support bar 726 is rigidly, perpendicularly mounted to vertical post 708. Each end of bar 726 terminates in right pads 728, 730, respectively, for restraining the back of the leg immediately behind the knee.

The top of post 708 inclines rearwardly and supports a trianguloid-shaped seat 732 for restraining the rear pelvic area and hips of the subject. Belt 734 is releasably attached to the upper corners of seat 732 for restraining the front pelvic area and hips of the subject. To use apparatus 700, the subject locates steps onto platform 704 with the feet of the subject over footprint indentations 716, 718. The left leg is located between pads 712, 722 and pad 728 and the right leg is located between pads 714, 724 and pad 730. Belt 732 is located around the front, lower waist area and affixed to seat 732. As a result, the lower body of the subject is restrained. The subject can now be instructed to bend to perform lumbar spine motion studies and the subject can be axially rotated about an axis coaxial with post 708 and the subject's spine when the spine is erect to place the spine in the proper position, i.e., in alignment with the fluoroscope for the motion studies.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. Apparatus for generating successive video images of a moving bone of a spine of a subject comprising:
    a fluoroscope including
        means, including a fluoroscopic x-ray tube, for radiating x-rays toward the moving bone;
        means, including a control, for controlling the operation of the fluoroscope and the radiation of x-rays by the fluoroscopic x-ray tube; and
        means, including an image intensifier, for generating a fluoroscopic image of the moving bone from x-rays radiated by the fluoroscopic x-ray tube toward the image intensifier, the moving bone being located between the fluoroscopic x-ray tube and the image intensifier in the path of the x-rays radiated by the fluoroscopic x-ray tube toward the image intensifier, said image intensifier spaced from the fluoroscopic x-ray tube to permit movement of the bone therebetween;
    means for detecting the fluoroscopic image of the moving bone generated by the image intensifier and converting the detected image of the moving bone into successive video images of the moving bone in various positions;

means for recording the successive video images; and means for displaying the recorded successive video images of the moving bone as the images are being generated by the image intensifier, said displaying means being located adjacent the fluoroscope adapted to be viewed by an operator permitting the operator to selectively observe and position the bone between the fluoroscopic x-ray tube and the image intensifier in response to images displayed on the displaying means; and means for immobilizing the lower body of the subject whereby only the spine is substantially moved during the generation of succession video images thereof.

2. Apparatus of claim 1 further comprising a crisscrossed grid adapted to be located adjacent the image intensifier between the bone and the image intensifier and adapted to enhance the image of the bone generated by the image intensifier as the bone moves by absorbing radiation directed toward the image intensifier which is not substantially perpendicular to the image intensifier.

3. Apparatus of claim 2 further comprising a table and means for supporting the fluoroscopic x-ray tube on the table such that the fluoroscopic x-ray tube is selectively tiltable with respect to the table so that the angle of the x-rays radiated by the fluoroscopic x-ray tube and impinging on the bone and the image intensifier is selectable.

4. Apparatus of claim 3 further comprising a first display connected to the control and located adjacent the means for monitoring for indicating the intensity of the exposure of the bone to x-rays generated by the fluoroscopic x-ray tube and a second display connected to the control and located adjacent the monitor for indicating the duration of the exposure of the bone to x-rays generated by the fluoroscopic x-ray tube.

5. Apparatus of claim 4 further comprising a remote monitor connected to the recording means for displaying the recorded successive video images as the images are being generated by the image intensifier, said remote monitor being located adjacent the control adapted to be viewed by a technician so that the technician is able to adjust the control in response to image displayed on the remote monitor.

6. Apparatus of claim 1 wherein the detecting means includes means for detecting a still image and for converting the still image into successive still images and wherein the recording means includes means for recording the successive still images.

7. Apparatus of claim 6 wherein the recording means includes means for recording the successive video images interlaced with the successive still images.

8. The apparatus of claim 1 wherein the detecting means comprises a video camera and the recording means comprises a video recorder.

9. Method for generating successive video images on a monitor of a bone comprising the steps of:
providing a fluoroscope;
positioning a bone within the fluoroscope;
moving the bone;
generating fluoroscopic images of he moving bone;
detecting the generated fluoroscopic images of the moving bone;
converting the detected images of the moving bone into successive video images of the moving bone;
recording the successive video images of the moving bone;
displaying the recorded successive video images of the moving bone as the fluoroscopic images are being generated;
positioning the bone within the fluoroscope in response to images displayed on the monitor;
moving the fluoroscope to track movement of the bone thereby producing successive video images of the bone as it moves; and
interlacing still images with the recorded successive video images.

10. Apparatus for analyzing the flexure of a joint between firs and second bones resulting from movement of the bones comprising:
means for creating at least two successive video images representative of the relative movement of the bones and the resulting flexure of the joint, said means for creating comprising a fluoroscopic system adapted to produce successive images of the joint and the bones as the joint is flexed and the bones are correspondingly moved, means for detecting the fluoroscopic images and means for recording the detected sequence of fluoroscopic images; and
means for comparing the successive video images to a reference representation corresponding to a reference movement of the first bone with respect to the second bone and the resulting flexure of the joint.

11. Apparatus of claim 10 wherein said fluoroscopic system comprises:
mean for providing radiation toward the joint to be analyzed;
means, located adjacent a side of the joint opposite the means for providing, for intensifying the provided radiation and for generating the image of the joint therefrom;
a crisscrossed grid located between the means for intensifying and the joint adapted to enhance the image of the joint generated by the means for intensifying.

12. The apparatus of claim 10 wherein the detecting means comprises a video camera and the recording means comprises a video recorder.

13. The apparatus of claim 10 wherein the fluoroscopic system has an x-ray tube and further comprising a table and means for supporting the tube on the table such that the tube is tiltable with respect to the table so that the angle of the x-rays radiated by the tube and impinging on the bones is selectable.

14. Apparatus for analyzing the flexure of a joint between first and second bones resulting from movement of the bones comprising:
means for immobilizing in at least one plane the first bone whereby only the second bone is substantially moved during flexure of the joint;
means for creating at least two successive video images of the relative movement of the bones and the corresponding flexing of the joint;
means for designating a reference point on the first bone on each video image and a monitoring point on the second bone in each video image; and
means for generating a representation corresponding to the pattern of movement of the monitoring point with respect to the reference point whereby only the second bone is substantially moved during flexure of he joint.

15. Apparatus of claim 14 further comprising:

means for storing a reference representation corresponding to a reference movement of the first bone with respect to the second bone and the resulting flexure of the joint; and means for comparing the reference representation to a present representation.

16. Apparatus of claim 15 further comprising means for providing an alarm when the difference between the reference representation and the present representation is greater than a predetermined limit.

17. Apparatus of claim 15 wherein the reference representation and the present representation comprise equations of the patterns of movement of the monitoring point with respect to the reference point and wherein the means for comparing includes means for determining the difference between coefficients of the equations.

18. Apparatus of claim 15 wherein the reference representation and the present representation comprise graphs of the movement of the monitoring point with respect to the reference point and wherein the means for comparing determines the difference between slopes of the graphs.

19. Apparatus of claim 15 further comprising an image memory and an analog-to-digital converter adapted to convert the video images into corresponding digital information and adapted to store the corresponding digital information in the image memory; a reference memory having digital information corresponding to the reference representation; and a central processing unit adapted to compare the corresponding digital information stored in the image memory to the reference representation stored in the reference memory.

20. Apparatus of claim 15 wherein said means for generating includes means for calculating, from the video images, the minimum and maximum angles between the first and second bones and said means for comparing includes means for determining differences between the minimum and maximum angles as compared to minimum and maximum reference angles, respectively, stored in the means for storing.

21. Apparatus of claim 14 wherein said means for creating comprises a fluoroscopic system adapted to produce images of the joint and the bones as the bones are moved resulting in flexure of the joint, a video camera adapted to detect the fluoroscopic images and a video recorder adapted to record the detected fluoroscopic images.

22. Apparatus of claim 21 wherein said fluoroscopic system comprises:
means for providing radiation toward the joint to be evaluated;
means, located adjacent a side of the joint opposite the means for providing, for intensifying the provided radiation and for generating said images of the joint therefrom;
a crisscrossed grid located between the means for intensifying and the joint adapted to enhance the image of the joint generated by the means for intensifying.

23. Apparatus of claim 21 wherein said means for designating comprises a video monitor adapted to display the detected fluoroscopic images recorded in the video recorder and a light pen connected to the video monitor adapted to indicate the reference point on the first bone and monitoring point on the second bone.

24. Apparatus of claim 14 for use with a human subject wherein said means for immobilizing comprises means for engaging the legs of the subject to prevent movement thereof and for permitting lumbar spine flexing and means for rotating the subject and said engaging means about an axis coaxial with the subject's spine when the subject is substantially erect.

25. Apparatus for analyzing the flexure of a joint between first and second bones resulting from movement of the bones comprising:
means for generating, from at least two successive video reference images of the movement of the bones and the resulting flexure of the joint, a reference representation corresponding thereto;
means for generating from at least two successive video present images of the movement of the bones and the resulting flexure of the joint, a present representation corresponding thereto;
means for comparing the reference representation to the present representation; and
wherein each of said means for generating comprises a fluoroscopic system adapted to produce images of the joint and the bones as the joint is flexed and the bones are correspondingly moved, a video camera adapted to detect the fluoroscopic images and a video recorder adapted to record the detected fluoroscopic images.

26. A fluoroscopic system comprising:
means for providing radiation toward a joint between first and second bones to be evaluated;
means, located adjacent a side of the joint opposite the means for providing, for intensifying the provided radiation and for generating an image of the object therefrom;
a crisscrossed grid adapted to be located between the means for intensifying and the object adapted to enhance the image of the object generated by the means for intensifying;
means for recording at least two successive images generated by said intensifying means, said images representing the movement of the bones and the resulting flexure of the joint; and
means for comparing the successive images to a reference representation corresponding to a desired or previous movement of the first bone with respect to the second bone and the resulting flexure of the joint.

27. The system of claim 26 wherein said means for providing comprises an x-ray tube and said means for intensifying comprises an image intensifier.

28. The system of claim 26 further comprising means for immobilizing the first bone whereby only the second bone is substantially moved.

29. In a video fluoroscopic system including means for providing radiation toward an object to be evaluated during movement ad means adapted to be located adjacent a side of the object opposite the means for providing, for intensifying the provided radiation and for generating an image of the object therefrom, the improvement comprising:
a crisscrossed grid of radiopaque material adapted to enhance the image of the object generated by the means for intensifying; and
means for supporting said grid on the means for intensifying between the means for intensifying and the object wherein said means for supporting comprises a pair of opposing tracks mounted externally on the means for intensifying, said grid positioned within the opposing tracks for selective, slidable movement.

30. Method for analyzing the movement of a joint between first and second bones comprising the steps of:
creating at least two successive video images of the movement of the bones by producing fluoroscopic images of the joint and the bones as the bones are moved, and detecting the fluoroscopic images and recording the detected fluoroscopic images;
determining differences between the successive video images as compared to a reference representation corresponding to a reference movement of the first bone with respect to the second bone.

31. Method of claim 30 wherein said step of creating comprises the step of using a fluoroscopic system comprising:
means for providing radiation toward the joint to be evaluated;
means, located adjacent a side of the joint opposite the providing, for intensifying the provided radiation and for generating said images of the joint therefrom;
a crisscrossed grid located between the intensifying means and the joint adapted to enhance the image of the joint generated by the intensifying means.

32. Method for analyzing the movement of first and second bones connected by a joint comprising the steps of:
moving the first bone with respect to the second bone thereby to flex the joint;
creating at least two successive video images while moving the bones by producing fluoroscopic images of the joint and the bones as the bones are moved resulting in flexure of the joint, by detecting the fluoroscopic images and by recording the detected fluoroscopic images;
designating a reference point on the first bone in each video image and a monitoring point on the second bone in each video image; and
generating a present representation corresponding to the pattern of movement of the monitoring point with respect to the reference point.

33. Method of claim 32 further comprising steps of:
storing a reference representation corresponding to a reference movement of the first bone with respect to the second bone; and
determining differences between the reference representation as compared to a present representation.

34. Method of claim 33 further comprising the step of providing an alarm when the difference between the reference representation and the present representation is greater than a predetermined limit.

35. Method of claim 34 further comprising the steps of storing digital information corresponding to the reference representation into a reference memory, converting the images into corresponding digital information and storing the corresponding digital information in an image memory; and comparing, by using a central processing unit, the corresponding digital information stored in the image memory to the reference representation stored in the reference memory.

36. Method of claim 33 further comprising the step of calculating, from the video images, the minimum and maximum angles between the first and second bones and wherein said 37. Method of claim 33 further comprising the step of calculating, from the relative movement of the reference and monitoring points, the minimum and maximum angles between the first and second bones and wherein said determining step compares the minimum and maximum angles to minimum and maximum reference angles, respectively.

38. Method of claim 32 wherein said step of creating comprises using fluoroscopic system comprising:
means for providing radiation toward the joint to be evaluated;
means, located adjacent a side of the joint opposite the providing means, for intensifying the provided radiation and for generating an image of the joint therefrom;
a crisscrossed grid located between the intensifying means and the joint adapted to enhance the images of the joint generated by the intensifying means.

39. Method of claim 32 further comprising the step of immobilizing the first bone so that only the second bone is substantially moved.

40. Method for analyzing the movement of first and second bones comprising the steps of:
moving the bones;
generating, from at least two successive video reference images of the movement of the bones, a reference representation corresponding to reference images;
generating, from at least two successive video present images of the movement of the bones, a present representation corresponding to present images;
comparing the present representation to the reference representation; and
wherein each said generating step comprises using a fluoroscopic system adapted to produce images of the bones as the bones are moved, using a video camera adapted to detect the fluoroscopic images and using a video recorder adapted to record the detected images.

41. A fluoroscopic method comprising the steps of:
providing radiation toward first and second bones connected by a joint;
moving said bones with respect to each other thereby resulting in flexure of the joint;
intensifying the provided radiation by using an intensifier located adjacent a side of the joint opposite the provided radiation;
generating an image of the bones from the intensified radiation;
placing a crisscrossed grid located between the intensifier and the bones adapted to enhance the image of the joint generated by the intensifier;
recording at least two successive images illustrating movement of the bones and the resulting flexure of the joint; and
determining differences between the successive images as compared to a reference representation corresponding to a reference movement of the first bone with respect to the second bone and the resulting flexure of the joint.

42. The method of claim 41 further comprising the step of immobilizing the first bone so that only the second bone is substantially moved.

* * * * *

UNITED STATES PATENT AND TRADEMARK OFFICE
CERTIFICATE OF CORRECTION

PATENT NO. : 5,099,859
DATED : March 31, 1992
INVENTOR(S) : Gene D. Bell

It is certified that error appears in the above-identified patent and that said Letters Patent is hereby corrected as shown below:

Column 17, (claim 4), line 34, "monitoring" should be --displaying-- (per Examiner's Amendment E); line 37, "monitor" should be --means for displaying-- (per Examiner's Amendment E).

Column 17 (claim 5), line 46, "image" should be --images--.

Column 17 (claim 9), line 64, "he" should be --the--.

Column 18 (claim 10), line 14, "firs" should be --first--.

Column 18 (claim 14), line 61, "on" should be --in--; line 67, "he" should be --the--.

Column 20 (claim 29), line 54, "ad" should be --and--.

Column 21 (claim 36), line 64, after "said", the following language has been omitted:

--determining step compares the minimum and maximum angles to minimum and maximum reference angles, respectively, stored in a reference memory.--

Signed and Sealed this

Eighth Day of June, 1993

Attest:

MICHAEL K. KIRK

Attesting Officer

Acting Commissioner of Patents and Trademarks